(12) United States Patent
Liebsch et al.

(10) Patent No.: US 12,313,545 B2
(45) Date of Patent: May 27, 2025

(54) METHOD, ARRANGEMENT, COMPUTER PROGRAM PRODUCT AND SENSOR FOIL FOR DETECTING MICROORGANISMS ON A SURFACE

(71) Applicant: PreSens Precision Sensing GmbH, Regensburg (DE)

(72) Inventors: Gregor Liebsch, Obertraubling (DE); Achim Stangelmayer, Neuburg an der Donau (DE); Robert Meier, Nittendorf (DE)

(73) Assignee: PRESENS PRECISION SENSING GMBH, Regensburg (DE)

( * ) Notice: Subject to any disclaimer, the term of this patent is extended or adjusted under 35 U.S.C. 154(b) by 0 days.

(21) Appl. No.: 16/352,384

(22) Filed: Mar. 13, 2019

(65) Prior Publication Data

US 2019/0212269 A1    Jul. 11, 2019

Related U.S. Application Data

(63) Continuation of application No. PCT/IB2017/055727, filed on Sep. 21, 2017.

(30) Foreign Application Priority Data

Sep. 21, 2016  (EP) .................................... 16189897
Nov. 10, 2016  (EP) .................................... 16198160

(51) Int. Cl.
  *G01N 21/64*  (2006.01)
  *C09K 11/06*  (2006.01)
  (Continued)

(52) U.S. Cl.
  CPC .......... *G01N 21/6428* (2013.01); *C09K 11/06* (2013.01); *C12Q 1/04* (2013.01);
  (Continued)

(58) Field of Classification Search
  CPC ....... G01N 21/6428; G01N 2021/7786; G01N 2021/6434; C09K 11/06; C12Q 1/04
  See application file for complete search history.

(56) References Cited

U.S. PATENT DOCUMENTS

| 4,657,736 A | 4/1987 | Marsoner et al. |
| 6,395,506 B1 * | 5/2002 | Pitner ...................... C12Q 1/04 |
| | | 435/32 |

(Continued)

FOREIGN PATENT DOCUMENTS

WO    2013/122852 A1    8/2013

OTHER PUBLICATIONS

Babilas, In Vivo Phosphorescence Imaging of pO2 Using Planar Oxygen Sensors Microcirculation (2005) 12, 477-487 (Year: 2005).*

(Continued)

*Primary Examiner* — William H. Beisner
*Assistant Examiner* — Danielle B Henkel
(74) *Attorney, Agent, or Firm* — Patentbar International

(57) ABSTRACT

A method and an arrangement, for detecting microorganisms on a surface are disclosed. At least a portion of the surface is covered with a sensor foil in an airtight manner. An oxygen-permeable layer of the sensor foil is doped with an oxygen indicator dye, loaded with oxygen and faces the at least one portion of the surface. An excitation light passes through an oxygen-impermeable at least partially transparent read-out carrier layer of the foil to the dye in the oxygen-permeable layer which is then excited by the excitation light. An emission of the oxygen indicator dye) transmitted through the carrier layer is detected by a detection element over or after a period of time (t). The emission of the oxygen indicator dye from the oxygen-permeable layer is indicative of the amount of oxygen consumed by (Continued)

microorganisms from the oxygen-permeable layer covering the at least one portion of the surface.

8 Claims, 9 Drawing Sheets

(51) Int. Cl.
    *C12Q 1/04*     (2006.01)
    *G01N 21/77*     (2006.01)

(52) U.S. Cl.
    CPC ........... *G01N 2021/6434* (2013.01); *G01N 2021/7786* (2013.01)

(56) References Cited

U.S. PATENT DOCUMENTS

| | | | | |
|---|---|---|---|---|
| 6,602,716 | B1* | 8/2003 | Klimant | G01N 21/6428 250/200 |
| 2009/0146080 | A1* | 6/2009 | Liebsch | A61B 5/14556 250/484.4 |
| 2012/0145882 | A1 | 6/2012 | Stangelmayer | |
| 2014/0296112 | A1* | 10/2014 | O'Driscoll | G01J 3/0208 506/39 |

OTHER PUBLICATIONS

H. Tschiersch et al., Imaging Microbial Culture O2 Consumption, Genetic Engineering & Biotechnology News, Aug. 2014 (Year: 2014).*
VisiSens Webinar—Metabolic Activity Inside Micofluidics, presenssensors, http://www.youtube.com/watch?v=qJIRaqLVxnl, screenshots of slides 15-16, Jul. 9, 2015 (Year: 2015).*
VisiSens Webinar—02, pH & CO2 in Plants, Roots, and Soil, presenssensors, http://www.youtube.com/watch?v+CvF9bJ1xcCu, May 17, 2016 screen shots at timestamp 8:43, 8:45 & 20:37 (Year: 2016).*
Ochs et al. Cellular Oxygen Consumption in Microfluidic Devices Monitoring Oxygen Tensions with the VisiSens System, PreSens precision sensing Technical Report Mar. 2013 (Year: 2013).*
Kellner et al., Determination of Oxygen Gradients in Engineered Tissue Using a Fluorescent Sensor, Biotechnology and Bioengineering, vol. 80, No. 1 Oct. 5, 2002 (Year: 2002).*
Blossfeld et al., Quantitative imaging of rhizosphere pH and CO2 dynamics with planar optodes, Annals of Botany 112:267-276, Mar. 2013 (Year: 2013).*
International Search Report from PCT/IB2017/055727, filed Sep. 21, 2017, mailed Dec. 1, 2017.
Henning et al, An imaging method for oxygen distribution, respiration and photosynthesis at a microscopic level of resolution, New Phytologist, 2012, vol. 196, pp. 926-936.
Kuehl et al, Functional and structural imaging of phototrophic microbial communicates and symbioses, Aquatic Microbial Ecology, Sep. 18, 2008, vol. 53, pp. 99-118.

* cited by examiner

METHOD, ARRANGEMENT, COMPUTER PROGRAM PRODUCT AND SENSOR FOIL FOR DETECTING MICROORGANISMS ON A SURFACE

RELATED APPLICATIONS

This Application is a Continuation application of International Application PCT/IB2017/055727, filed on Sep. 21, 2017, which in turn claims priority to European Patent Applications EP16189897.8, filed Sep. 21, 2016 and EP16198160.0, filed Nov. 10, 2016, all of which are incorporated herein by reference in their entirety.

FIELD OF THE INVENTION

The invention relates to a method for detecting microorganisms on a surface.

Additionally, the invention relates to an arrangement for detecting microorganisms on a surface.

Moreover, the invention relates to a computer program for detecting microorganisms on a surface.

Finally, the invention relates to a sensor foil used for the detection of microorganisms on a surface.

BACKGROUND OF THE INVENTION

Methods, arrangements and devices for detecting microorganisms on antimicrobial surfaces, other surfaces, which are contacted by a plurality of people or animals, or surfaces, which are presumed to be contaminated by microorganisms are well known in prior art. For example, these devices and methods are applied to such as, but not limited to, various surfaces in hospitals, such as operating units and emergency units, intensive care units, premature infants stations, normal hospital units, surfaces of touch displays in public transport systems, such as for example busses, trains and planes, department stores, public and private buildings, such as for example nurseries, preschools, schools, libraries, canteens, restaurant kitchens, cafeterias, butcheries, etc. Furthermore, these devices and methods are applied to human beings and animals, in particular, but not limited to, human beings or animals with immune deficiencies, for example premature babies, senior people, cancer patients taking immunosuppressants, etc.

One known method is the paddle test, also called "set-off test" or "wipe test" ("Abklatschtest" in German). One disadvantage of the paddle test is the long duration from sampling the microorganisms from a surface to be inspected to the receiving the results, since it takes up to two days from the sampling to the test results. Another disadvantage of the paddle test is that the sample is transferred from the sampling site to an incubator in a laboratory. The detection of the sample is therefore not carried out in situ (on-site), which in turn means that it may take too long for the results, before the results are available, whereas the problem of, for example, germination still exists on-site, i.e. at the site of the surface to be inspected and detected. Still a further disadvantage of the paddle test is that there is no evaluation of the actual distribution of the microorganisms in situ, but rather an evaluation after the microorganisms of the original sample have been further grown or multiplied for a certain time, and thus the subsequent detection is no longer performed based on the original sample. Hence, conventional detection methods and arrangements are based on proliferation (cell division) and measure turbidity resulting from increased cell material (e.g., Biomerieux, Vitek and AST cards). This can lead to distortion of results, in particular with regard to the actual quantities and the actual distribution of the microorganisms at the sampling site.

Another known method is the coloring of the microorganisms for detection, wherein a sample preparation as well as post-processing are required, such as, for example, cleaning the location of the sampling, which makes the method cumbersome and inefficient.

SUMMARY OF THE INVENTION

It is therefore an object of the invention to provide a method for detecting microorganisms on a surface which is easy to carry out and provides the information about the presence, absence or vitality of microorganisms in a short period of time.

The above object is achieved by a method for detecting microorganisms on a surface. The method comprises the steps of:

attaching a sensor foil to at least a portion of the surface to be examined with in an airtight manner, wherein an oxygen-permeable layer of the sensor foil is doped with an oxygen indicator dye, loaded with oxygen and faces the at least one portion of the surface;

placing a detection element in optical relation to the sensor foil;

exciting the oxygen indicator dye in the oxygen-permeable layer with an excitation light through an oxygen-impermeable at least partially transparent read-out carrier layer of the sensor foil; and detecting an emission of the oxygen indicator dye transmitted through the oxygen-impermeable at least partially transparent read-out carrier layer of the sensor foil by the detection element over or after a period of time, wherein the emission of the oxygen indicator dye from the oxygen-permeable layer is indicative to the amount of oxygen consumed by microorganisms from the oxygen-permeable layer covering the at least one portion of the surface.

It is also an object of the invention to provide an arrangement for detecting microorganisms on a surface which is easy to use, simple and compact in construction and provides the information about the presence, absence or vitality of microorganisms in a short period of time.

The above object is achieved by an arrangement for detecting microorganisms on a surface, the arrangement comprising:

a sensor foil having an oxygen-permeable layer doped with an oxygen indicator dye and loaded with oxygen and an oxygen-impermeable, at least partially transparent read-out carrier layer which carries the oxygen-permeable layer, wherein the sensor foil is placed on at least a portion of the surface in an airtight manner;

a detection element is arranged in optical relation to the sensor foil for receiving an emission of the excited oxygen indicator dye in the oxygen-permeable layer transmitted through the oxygen-impermeable at least partially transparent read-out layer;

an evaluation unit for calculating a graphical or statistical representation of the received emission; and a display, connected to the evaluation unit, adapted to display a graphical or statistical representation of a concentration of the microorganisms on the surface being indicative to a presence of microorganisms on the at least one portion of the surface covered by the sensor foil.

A further object of the invention is to provide a computer program product disposed on a non-transitory computer readable medium for detecting microorganisms on a surface which is easy to use on stationary, mobile and/or integrated devices and provides an information about the presence, absence or vitality of microorganisms in a short period of time.

The above object is achieved by a computer program product for detecting microorganisms on a surface, wherein the computer program controls the computer to:

read data from a detector chip which is placed in optical relation to a sensor foil attached to at least a portion of the surface to be examined with its oxygen-permeable layer in an airtight manner, wherein the oxygen-permeable layer of the sensor foil is doped with an oxygen indicator dye, loaded with oxygen and faces the at least one portion of the surface, and an oxygen-impermeable at least partially transparent read-out carrier layer of the sensor foil faces the detector chip;

calculate from the read data an amount of the microorganisms and their distribution on at least one portion of the surface; and control a display to show a graphical or statistical representation of a concentration of the microorganisms on the surface, based on the detected emission, in or after defined time intervals.

Another object of the invention is to provide a sensor foil for detecting microorganisms on a surface which can be applied in situ to the surface to be tested, is easy to use and provides the information about the presence, absence or vitality of microorganisms in a short period of time.

The above object is achieved by a sensor foil for detecting microorganisms on a surface having:

an oxygen-permeable layer which is doped with an oxygen indicator dye and loaded with oxygen, wherein the oxygen-permeable layer is adapted to be attached to at least one portion of the surface in an airtight manner; and an oxygen-impermeable at least partially transparent read-out carrier layer adapted to carry the oxygen-permeable layer.

In an exemplary embodiment of the invention, a method for detecting microorganisms on a surface covered with microorganisms is provided. The method is as well applicable for tests showing the functionality of antibiotic surfaces. In the beginning, at least a portion of the surface to be examined is covered with a sensor foil. The sensor foil is attached to the surface to be examined in an airtight manner. In the context of the present invention, "air tight manner" means that the ingress of ambient air between the surface and a first free surface side of an oxygen-permeable layer of the sensor foil, which is in contact with the surface to be examined, is hindered and avoided. The oxygen-permeable layer of the sensor foil is doped with an oxygen indicator dye and loaded with oxygen, for example loaded at an ambient air oxygen level. The oxygen-permeable layer of the sensor foil faces the at least one portion of the surface to be examined. Next a detection element is placed in optical relation to the sensor foil.

For carrying out the detection of the presence or absence of microorganisms on the surface an excitation light is directed through an oxygen-impermeable at least partially transparent read-out carrier layer of the sensor foil and to illuminate the oxygen-permeable layer of the sensor foil with a required wavelength or wavelength spectrum to excite the oxygen indicator dye and optionally at least one reference dye. It is noted herein that in the context of the present invention, the property "at least partially transparent" of the read-out carrier layer means that the read-out carrier layer is at least partially transparent with regard to said excitation light. For reasons of conciseness the term "at least partially" is usually omitted in the description. The excitation light excites the oxygen indicator dye in the oxygen-permeable layer. An emission (light emission) of the oxygen indicator dye is transmitted through the oxygen-impermeable at least partially transparent read-out carrier layer of the sensor foil. The detection element samples over or after a period of time the emission of the oxygen indicator dye from the oxygen-permeable layer and emission indicative to the amount of oxygen consumed by microorganisms from the oxygen-permeable layer covering the at least one portion of the surface.

Such a method is easy to carry out and delivers fast and correct results in situ. In other words, the sensor foil is kept in ambient air of said at least one portion of the surface, so that the sensor foil is "loaded" with ambient air oxygen. The surface and the possible microorganisms on the surface of the sample (at least one portion of the surface) are covered in an airtight manner to be detected by means of the sensor foil, wherein re-oxygenation from ambient air is blocked and the possible microorganisms are covered or even sealed between one or more oxygen impermeable layers. The measurement with respect to oxygen consumption of possible microorganisms can start immediately. While the microorganisms "breathe" the oxygen out of the sensor foil, the oxygen sensor foil shows oxygen decrease in response to microorganisms respiration.

The results can be immediately viewed via a display of an embedded device, for example a mobile device, laptop, tablet, smartphone, cellular phone or the like. In order to make the emission viewable, the detector element can be a detector chip and part of a detection device and the emission of the oxygen indicator dye is imaged with a suitable optic on the detector chip.

According to a further embodiment of the invention, the detection element is a detector chip. The detector chip is directly attached to the at least partially transparent read-out carrier layer for receiving the emission of the oxygen indicator dye. No optics is needed to image the emission of the oxygen indicator dye onto the detector chip. The emission of the oxygen indicator dye is projected onto the detector chip. The detector chip can be equipped with an OLED in order to excite the sensor foil at the measurement site (surface to be examined for microorganisms). Thus, no further excitation light sources are needed, for example ring light around a detection element (for example, camera objective). The sensor foil response can be read-out with the naked eye, so that a user can directly see the presence or absence of microorganisms on the surface to be examined. Additionally, the sensor foil response can be read-out through an electronic detection element.

Note that throughout the specification, the term "microorganisms" means any oxygen-breathing organism or anaerobic organism. The term "in situ" means the place of the environment, i.e. the surface, to be inspected by the method, arrangement, computer program product or sensor foil of the present invention.

In all embodiments described above and in the following, any oxygen dissolved in the oxygen-permeable layer (sensitive polymer layer) of the sensor foil represents an "oxygen reservoir" which is consumed, if there are any oxygen-breathing microorganisms on the surface to be inspected due to respiration of the microorganisms. The oxygen indicator dye in the oxygen-permeable layer then responds to the change of oxygen in the oxygen-permeable layer.

In an exemplary embodiment the method comprises a step of post-processing the detected emission, so that the absence and presence and/or the amount of the microorganisms and their distribution and/or even types are determined in situ with respect to the at least one portion of the surface. Based on the detected emission, for example a computer-implemented software is used to analyze detected emission. Thus, the software processes the detected results from the raw sensor foil response for displaying and post-processing the detected results in more detail. For example, an exact determination can be made of the amount of the microorganisms and their distribution present on the surface of the sample. Regions (regions of interest (ROIs)) colonized by microorganisms can be depicted down to micrometer resolution. All this is carried out again in situ and immediately along with the detection process. For example, the post-processing can provide a graphical representation or statistical evaluation of the concentration of the microorganisms by way of a 2-dimensional image of the distribution of microorganisms on at least a portion of the surface. A further possibility is a plot showing the development of the concentration of the microorganisms or a statistical evaluation of colonies or microorganisms per surface area over time.

The detector chip can be coupled to the evaluation unit, which can be a separate or an embedded device with regard to the detector chip, wireless or via a cable. Thus, the detector chip "reads" the sensor foil in situ and immediately along with the detection process, i.e. the emission transmitted through the oxygen-impermeable transparent read-out carrier layer to the detector chip. The data from the detector chip are processed in situ and immediately along with the detection process or subsequently to the recording process.

In an exemplary embodiment the method comprises a step of determining the minimum inhibitory concentration (MIC) based on the detected emission.

In an exemplary embodiment of the invention, an arrangement for detecting microorganisms consuming oxygen on a surface is provided. The arrangement comprises a sensor foil for covering at least a portion of the surface to be examined, preferably in an airtight manner. The sensor foil is essentially composed of two layers. A first layer is an oxygen-permeable layer doped with an oxygen indicator dye and loaded with oxygen from the environment. The oxygen-permeable layer "loads" oxygen from said environment. A second layer is an oxygen-impermeable transparent read-out carrier layer for carrying the oxygen-permeable layer.

The sensor foil has two opposite free surface sides. The first free surface side is a free surface side of the oxygen-permeable layer. The second free surface side is a free surface side of the oxygen-impermeable transparent read-out carrier layer.

The oxygen-permeable layer contacts the surface to be examined with the first free surface side of the oxygen-permeable layer. A read-out surface side of the oxygen-permeable layer, which side is opposite of the first free surface side in the oxygen-permeable layer, is covered with the oxygen-impermeable transparent read-out carrier layer. Hence, the first free surface side of the oxygen-permeable layer is an oxygen-permeable contact side towards the possible microorganisms, and the second free surface side of the oxygen-impermeable transparent read-out carrier layer is an oxygen-impermeable transparent read-out side towards the detection element.

Preferably, the arrangement comprises a detection element which is arranged in optical relation to the sensor foil for receiving an emission of the excited oxygen indicator dye in the oxygen-permeable layer, wherein the emission is transmitted through the oxygen-impermeable transparent read-out layer. Preferably, an evaluation unit is in communicative connection with the detection element, for calculating at least a graphical or statistical representation of the received emission. Preferably, a display, which is connected to the evaluation unit, is adapted to display a graphical representation of a concentration of the microorganisms on the surface or a statistical representation of the amount of microorganisms per surface. The graphical representation is indicative to a presence of microorganisms on the at least one portion of the surface covered by the sensor foil.

According to an embodiment of the invention, a light source is provided and adapted to illuminate at least a portion of the sensor foil attached to at least a portion of the surface to excite the oxygen indicator dye in the oxygen-permeable layer. The emission transmitted through the oxygen-impermeable transparent read-out carrier layer is detected by the detection element (sensor chip) and processed by the evaluation unit.

The arrangement as described above has the advantage that it is easy to use in situ, simple and compact in construction and delivers fast and correct results in situ.

In an exemplary embodiment, the detection element is a sensor chip to detect the emission of the oxygen indicator dye which is transmitted through the oxygen-impermeable transparent read-out carrier layer of the sensor foil. According to one possible embodiment of the invention, the sensor chip is directly attached to the transparent read-out carrier layer for receiving the emission of the oxygen indicator dye. The sensor chip can be in a communicative connection with the evaluation unit. Any communicative connection which is known in the art can be realized.

The sensor foil can be equipped with an OLED (organic light emitting diode) in order to excite the sensor foil at the measurement site (surface to be examined for microorganisms). Thus, no further excitation light sources are needed, for example ring light around a detection element (for example, camera objective). Omitting a detector chip, the sensor foil response can be read-out with the naked eye, so that a user can directly see the presence or absence of microorganisms on the surface to be examined. Additionally, the sensor foil response can be read-out through an electronic detection element. The OLED can be arranged in a line or in an array. The OLED is flexible and can be directly attached to the sensor foil which is attached to the surface to be examined for possible microorganisms. In this case, no optics, such as for example a camera, is required between the detector chip and the OLED or OLEDs equipped sensor foil on the one hand and the surface to be tested on the other hand. Additionally, the sensor foil response can be read-out through an electronic detection element.

In another embodiment, the detector chip is a CMOS (complementary metal-oxide-semiconductor). Thus, the detection by means of the detector chip is also easy to carry out, i.e. in situ (on-site) with respect to the location of the surface or sample to be inspected for possible microorganisms, i.e. without preparation or follow-up at the sample location. The handling of such a detection element or detector chip can be quickly learned by untrained personnel and provides objectified results. The arrangement according to the invention with the detection element or detection device is mobile-compatible, i.e. can be integrated or connected with a mobile or cellular phone or any other smart device.

According to another embodiment of the invention, the detection element is a detection device. The detection device is composed of at least one detector chip and an optic, which are held in position by a housing. The optic images the emission of the oxygen indicator dye, transmitted through the oxygen-impermeable transparent read-out layer of the sensor foil, onto the detector chip. The detector chip is in a communicative connection with the evaluation unit.

In an exemplary embodiment, the detection element or detection device is attached in a fixed or detachable manner to the second free surface side of the oxygen-impermeable transparent read-out layer of the sensor foil.

In an exemplary embodiment, the detection element or detection device encompasses at least one light source (light emitting element) adapted to direct an excitation light through the oxygen-impermeable transparent read-out carrier layer of the sensor foil to the oxygen-permeable layer of the sensor foil, so that the oxygen indicator dye in the oxygen-permeable layer is excited by the excitation light and emits the emission. This emission is then detected in any embodiment as described above by means of said detection element or device. The detection element or device is removable mounted to a second free surface side of the oxygen-impermeable transparent read-out layer of the sensor foil.

In an exemplary embodiment, the detection element or device has the at least one light source, the detector chip and any further optical elements integrated in the housing, which provides an arrangement that is even more easy to use, simple and compact in construction and delivers fast and correct results.

In an alternative embodiment, the sensor foil is read-out only via the camera and not by a detection element as described above. In case a camera is used, as described above, the camera "reads" the sensor foil in situ and immediately along with the detection process, i.e. the emission transmitted through the oxygen-impermeable transparent read-out carrier layer outside the environment and sensor foil to the detection element or device is imaged and digitally represented in situ and immediately along with the detection process.

In an exemplary embodiment, the detection element or detector chip is connected with an evaluation unit for post-processing the detected emission, i.e. for evaluating the amount of oxygen detected by the detection element over a period of time. For example, types and/or amounts of the microorganisms are determined with respect to the surface and based on the detected emission, for example by a computer-implemented software in the evaluation unit. This is carried out immediately along with the detection and in situ with respect to the surface to be inspected for possible microorganisms. Thus, regions colonized by microorganisms can be depicted and detected down to micrometer resolution.

In an exemplary embodiment, the oxygen-permeable layer of the sensor foil is doped with at least one reference dye for determining at least one parameter of the microorganisms, so that an emission of the at least one reference dye is transmitted through the oxygen-impermeable transparent read-out carrier layer and is detected by the detection element. Different dyes can be used for determining different properties the microorganisms to be detected, thereby characterizing the microorganisms.

According to the invention, a computer program product, disposed on a non-transitory computer readable medium, is used for detecting microorganisms on a surface. The computer program product comprises at last one computer executable process step operable to control a computer. Firstly, data are read from a detector chip which is placed in optical relation to a sensor foil. The sensor foil covers at least a portion of the surface to be examined in an airtight manner. An oxygen-permeable layer of the sensor foil is doped with an oxygen indicator dye, loaded with oxygen and faces the at least one portion of the surface. An oxygen-impermeable transparent read-out carrier layer of the sensor foil faces the detector chip. Preferably, with the computer program a calculation of the amount of the microorganisms and their distribution on at least one portion of the surface is carried out from the read data. Preferably, the computer program controls a display in order to show a graphical or statistical representation of a concentration of the microorganisms on the surface in or after defined time intervals.

In one embodiment, the computer program allows that at least one image window can be defined on the detector chip. Accordingly, the data are only read from the at least one image window in order to calculate the amount of the microorganisms as described above.

According to the invention, an inventive sensor foil for detecting microorganisms on a surface has an oxygen-permeable layer carried by an oxygen-impermeable transparent read-out carrier layer adapted to carry the oxygen-permeable layer. The oxygen-permeable layer is doped with an oxygen indicator dye and loaded with oxygen. The oxygen-permeable layer is adapted to be attached to at least one portion of the surface in an airtight manner.

It is advantageous if the sensor foil is bendable and flexible. The sensor foil can be adapted and attached to any topology of the surface.

In an exemplary embodiment, the oxygen-permeable layer of the sensor foil comprises polyvinyl chloride. The oxygen-impermeable transparent read-out carrier layer of the sensor foil comprises polyester. The oxygen indicator dye is fluorescent, phosphorescent, luminescent, colormetric and/or has another optical property changing over time with respiration of oxygen by the microorganisms, for example, but not limited to, ruthenium metal-ligand complexes or metalloporphyrins. The oxygen-permeable layer of the sensor foil can have combinations of oxygen indicator dye and reference dyes which allows to carry out ratiometric measurements of microorganisms on various surfaces.

In further embodiments, the oxygen-permeable layer of the sensor foil is antimicrobial and/or antibiotic. For this, the oxygen-permeable layer of the sensor foil is treated and/or functionalized, for example coated or soaked with antibiotics in order to determine the degree of effectiveness of the antibiotics in a series of samples covered with the thus treated sensor foil, as will be described in more detail later. In order to distinguish between the functionality of the tested antibiotics (or other substance), a first free surface side of the oxygen-permeable layer of sensor foil carries a regular pattern of a plurality of fields. Each field, except one, contains a different type of an antibiotic. The field with no antibiotic is used as a reference field.

In general, the method, arrangement, computer program product and sensor foil of the present invention can be applied to an antimicrobial or antibiotic surface of an item, human being or animal, as described above in the background art section which surface is to be inspected with regard to potential microorganisms thereon. Thus, the method and the arrangement according to the present invention enable detection of any oxygen respiring or anaerobic microorganisms on any surface via monitoring their respiration with an oxygen sensor provided by the sensor foil of the method and arrangement as described above. In contrast to the prior art, no proliferation is necessary, since the $O_2$ consumption of any possibly existing microorganisms is measured, which is carried out very fast. However, a typical proliferation is present, which depends on the surrounding conditions the microorganisms are living in.

The surface with potential microorganisms can be a sample to be detected and can be examined in situ, within a short time period, typically 1 to 5 minutes, and without sample preparation. The size of the surface or surface region to be monitored and detected can be any size, for example from a few $\mu m^2$ up to $cm^2$ range. Even small surface regions with microorganisms ("hot spots") on relatively big surfaces can be identified and detected by the method, arrangement, computer program product and sensor foil of the present invention. The surface to be monitored and detected can also have any shape or topology.

Further in general, the surface to be monitored is covered, in particular airtight sealed, with the oxygen sensor foil of the invention. The sensor foil can be a thin film. The shape of the sensor foil can be flexible and bendable, so that even uneven surfaces can be detected for microorganisms. As described above, an oxygen indicator dye doped and oxygen-permeable layer (oxygen sensitive layer) is fixed onto an oxygen-impermeable transparent read-out carrier layer (support). The oxygen content in the sensitive layer is equivalent to the oxygen partial pressure of the contacting phase or sample of the environment to be inspected for possible microorganisms. Thus, oxygen is sensed by means of the sensor foil without oxygen consumption. Any detected oxygen change can be directly allocated to respiration of microorganisms.

The method, arrangement, computer program product and sensor foil of the present invention can also be used for testing whether an antimicrobially coated surface kills germs (as microorganisms) or an antimicrobially (pre)treated surface is germ-free or at least minimally contaminated by germs. For this, the surface can, for example, be antimicrobially coated. Furthermore, for this, the surface is either directly examined and measured with regard to the presence and/or distribution of germs (microorganisms) as described above, or the antimicrobial surface is intentionally contaminated with germs or other microorganisms, and the effectiveness of the killing of germs (microorganisms) or the reduction of germination by the antimicrobial surface is monitored.

In further embodiments of the inventive method and arrangement, the response of the microorganisms is "influenced". In one embodiment, a temperature of at least a part of the surface to be examined is changed, for example by a relatively moderate heating, for example by infrared (IR) or an internal tempering system in the sensor foil, in order to change an activity degree of the microorganisms, for example so that the microorganisms become more active. In another embodiment, at least a part of the surface to be examined is treated for example with UV radiation, so that the microorganisms are possibly killed; for example, the UV radiation is emitted from at least a part of the sensor foil. All changes of temperature can, for example, be carried out by at least a part of the sensor foil. In still another embodiment, at least one respiratory decoupler is placed on the oxygen-permeable layer of the sensor foil, so that the microorganisms are able to consume more oxygen (in comparison to that no respiratory decoupler is used) and a faster response time is achieved. These respiratory decouplers can be selected specifically for certain microorganisms, so that specific types of microorganisms can be targeted. In still another embodiment, specific antibiotics, as described above and below, for certain microorganisms are selected in such a way that specific types of microorganisms can be selectively killed or resistant microorganisms can be detected.

A further advantage, in addition to the other advantages mentioned, is that the sensor foil of the method and arrangement of the present invention does not require electricity.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limiting to the present invention, and wherein.

DETAILED DESCRIPTION OF THE PREFERRED EMBODIMENTS

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Figure 1:
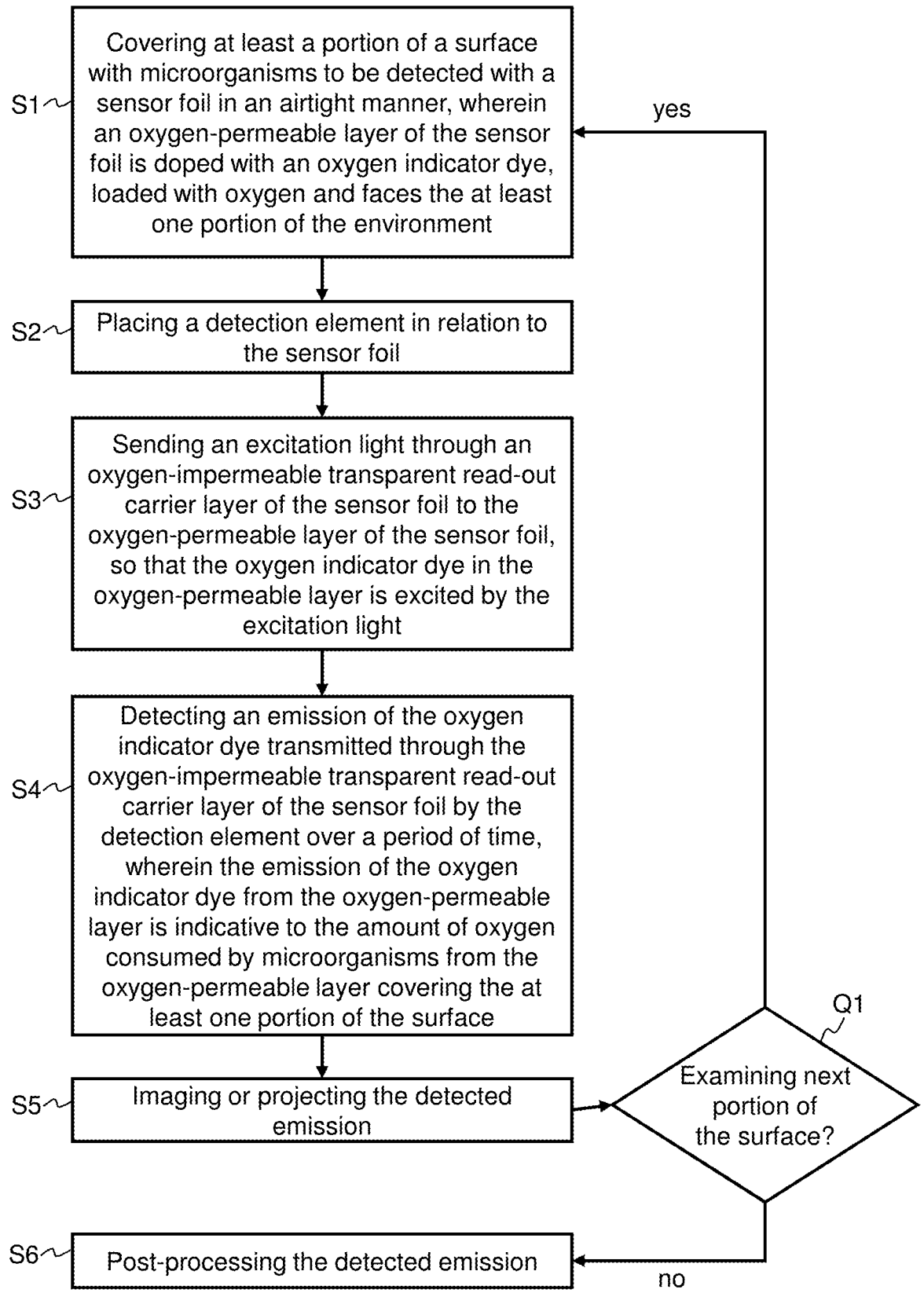
FIG. 1 is a flowchart of a method for detecting microorganisms according to an embodiment to the present invention.

FIG. 1 is a flowchart of an embodiment of a method for detecting microorganisms 3 consuming oxygen 4. In step S1, at least a portion of the surface 2 to be detected or examined is covered with a sensor foil 20 in an airtight manner, wherein an oxygen-permeable layer 21 of the sensor foil 20 is doped with an oxygen indicator dye 26, loaded with oxygen 4 and faces the at least one portion of the environment 2.

In step S2, a detection element 30 is placed in optical relation to the sensor foil 20.

In step S3, an excitation light 32 is sent through an oxygen-impermeable transparent read-out carrier layer 24 of the sensor foil 20 to the oxygen-permeable layer 21 of the sensor foil 20, to the oxygen indicator dye 26 in the oxygen-permeable layer 21 which oxygen indicator dye 26 is then excited by the excitation light 32.

In step S4, an emission 27 of the oxygen indicator dye 26 transmitted through the oxygen-impermeable transparent read-out carrier layer 24 of the sensor foil 20 is detected by the detection element 30 over or after a period of time t, wherein the emission 27 of the oxygen indicator dye 26 from the oxygen-permeable layer 21 is indicative to the amount of oxygen 4 consumed by microorganisms 3 from the oxygen-permeable layer 21 covering the at least one portion of the surface 2.

In an optional step S5, the detected emission 27 is imaged or recorded, for example with a sensor chip 34 of the detection element 30 for detecting the emission 27.

In an optional query Q1, it is determined whether a next or another portion of the surface 2 should be examined; if so, step S1 to S4 and optionally S5 are repeated; if not, the method is terminated, or in an optional step S6, the detected emission 27 is post-processed, so that the amount and/or the distribution of the microorganisms 3 is/are determined in situ with respect to the at least one (current) portion on the surface 2 and based on the detected emission 27. The post-processing can be done, for example, by a computer-implemented software. Such a query Q1 can be useful in case more than one sample as portion of the surface 2 shall be examined for possible microorganisms 3.

During step S4 or thereafter, for example the minimum inhibitory concentration (MIC) based on the detected emission 27 can be determined.

Figure 2:
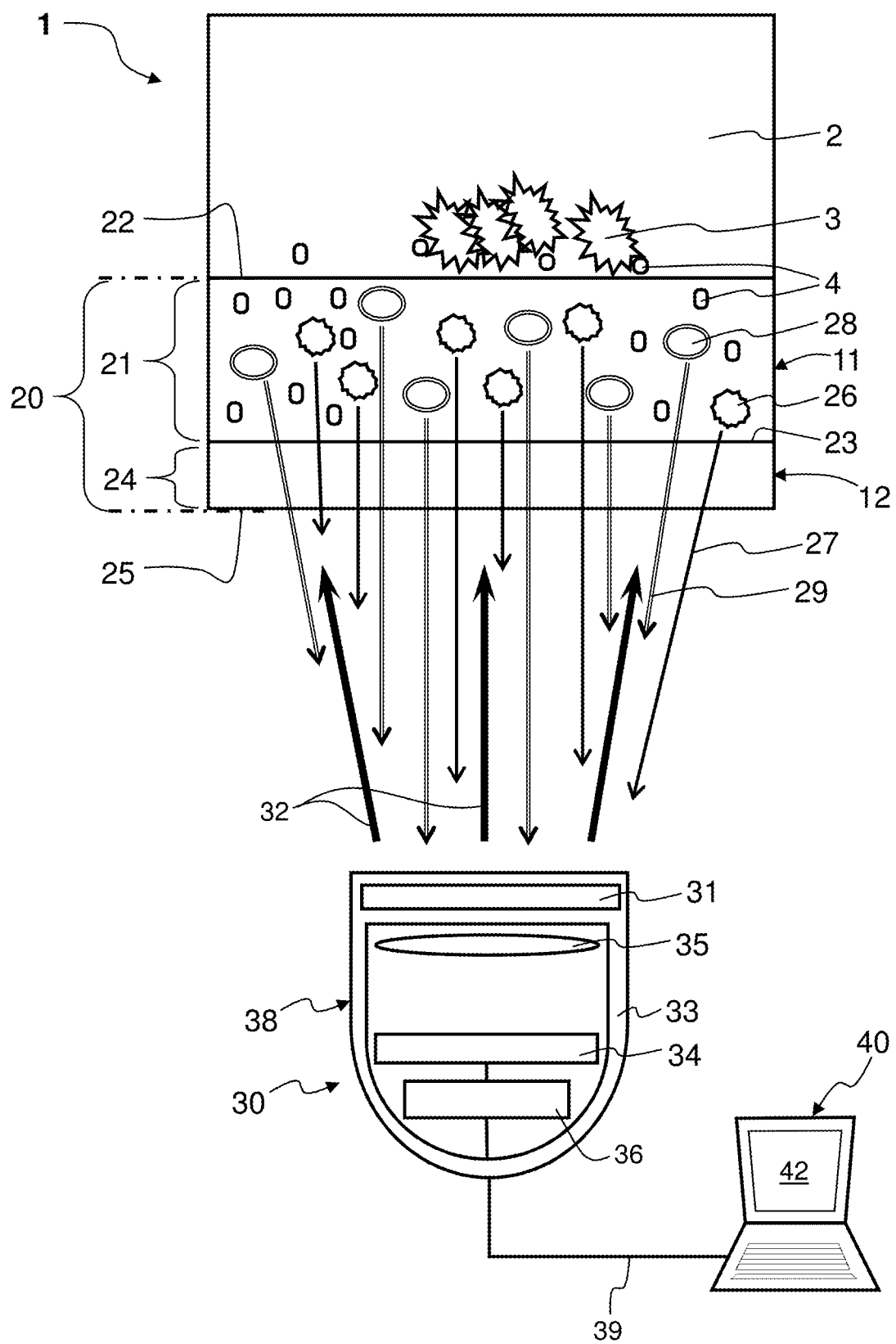
FIG. 2 is a schematic view of an arrangement for detecting microorganisms according to an embodiment to the present invention.

FIG. 2 shows a schematic view of an arrangement 1 for detecting microorganisms 3 consuming oxygen 4 according to an embodiment to the present invention.

The arrangement 1 provides a sensor foil 20 for covering at least a portion of the environment 2 to be detected. The sensor foil 20 is essentially composed of a first layer 11 and a second layer 12. The first layer 11 is an oxygen-permeable layer 21 doped with an oxygen indicator dye 26 and loaded with oxygen 4. The oxygen-permeable layer 21 "loads" oxygen ($O_2$) 4 from the environment and thus represents an oxygen reservoir inside the sensor foil 20 due to oxygen solubility in the polymer used. A second layer 12 is an oxygen-impermeable transparent read-out carrier layer 24 for carrying the oxygen-permeable layer 21.

The sensor foil 20 has a first free surface side 22 and a second free surface side 25. The first free surface side 22 is a free surface side of the oxygen-permeable layer 21 and is used to contact at least a portion of the surface 2. The second free surface side 25 is a free surface side of the oxygen-impermeable transparent read-out carrier layer 24.

A read-out surface side 23 of the oxygen-permeable layer 21 is covered with the oxygen-impermeable transparent read-out carrier layer 24. The read-out surface side 23 is opposite to the second free surface side 25 with regard to the oxygen-impermeable transparent read-out carrier layer 24.

In an embodiment of the invention, the arrangement 1 comprises a detection element 30 adapted to illuminate at least a portion of the sensor foil 20 attached to at least a portion of the surface 2 to excite the oxygen indicator dye 26 in the oxygen-permeable layer 21 and to detect an emission 27 transmitted through the oxygen-impermeable transparent read-out layer 24.

Hence, the first free surface side 22 of the oxygen-permeable layer 21 is an oxygen-permeable contact side towards the possible microorganisms 3, and the second free surface side 25 of the oxygen-impermeable transparent read-out carrier layer 24 is an oxygen-impermeable transparent read-out side towards the detection element 30.

In an embodiment of the invention, the arrangement 1 shown here, comprises a display 42 adapted to show a distribution of microorganisms 3, for example a 2-dimensional distribution, on the at least one portion of the sample 2. A statistical analysis of microorganisms per area on the surface is possible with the use of an evaluation unit 40 in communicative connection with the display 42. The detected emission 27 is indicative to a presence of microorganisms 3 on the at least one portion of the surface 2.

In the embodiment shown here, the detection element 30 is a detection device 38. The detection device 38 has at least one detector chip 34. The detector chip 34 and an optic 35 are held in position by a housing 33. The detector chip 34 is used to detect the emission 27 of the oxygen indicator dye 26 which is transmitted through the oxygen-impermeable transparent read-out carrier layer 24 of the sensor foil 20. The optic 35 can as well be held in position by the housing 33. The optic 35 images the emission 27 of the oxygen indicator dye 26, which emission 27 is transmitted through the oxygen-impermeable transparent read-out layer 24 of the sensor foil 20, onto the detector chip 34. In the embodiment shown here, the detector chip 34 is in a communicative connection 39 with an evaluation unit 40. In the embodiment shown here, the evaluation unit 40 is a laptop with a display 42. It should be noted the laptop does not limit the present invention, but any mobile device (evaluation unit 40 with display 42) can be used to practice the invention.

In FIG. 2 the housing 33 comprises at least one light source 31 (light emitting element) adapted to direct an excitation light 32 through the oxygen-impermeable transparent read-out carrier layer 24 of the sensor foil 20 to the oxygen-permeable layer 21 of the sensor foil 20. The oxygen indicator dye 26 in the oxygen-permeable layer 21 is excited by the excitation light 32 and emits the emission 27. However, the detection element 30 can encompass more than one light source 31 (not shown in drawings). In the embodiment shown here, the at least one light source 31 is a part of the housing 33 which is not limiting the invention, since another construction of a light source 31 can be used.

In an embodiment of the invention, the detection element 30 is connected with the evaluation unit 40 by a connection 35. A transmission circuitry 36 can be assigned to the detector chip 34. The evaluation unit 40 is used to evaluate the amount of oxygen 4 detected by the detection element 30 over or after a period of time t. By way of non-limiting example, the evaluation unit 40 illustrated in FIG. 2 is configured with the above-mentioned display 42 adapted to show a distribution of microorganisms 3. It is obvious to a person skilled in the art that the display 42 can be provided as a separate device or integrated in the detection element 30 (see FIG. 4) or integrated in any other separate device, for example a smart device as mentioned above. The connection 35 between the detection element 30 and the evaluation unit 40 can comprise at least one cable or can be a wireless connection.

In an embodiment of the invention, the oxygen-permeable layer 21 of the sensor foil 20 for determining at least one parameter of the microorganisms 3 is doped with at least one reference dye 28 so that an emission 29 of the at least one reference dye 28 is transmitted through the oxygen-impermeable transparent read-out carrier layer 24 and is detected by the detection element 30.

Figure 3:
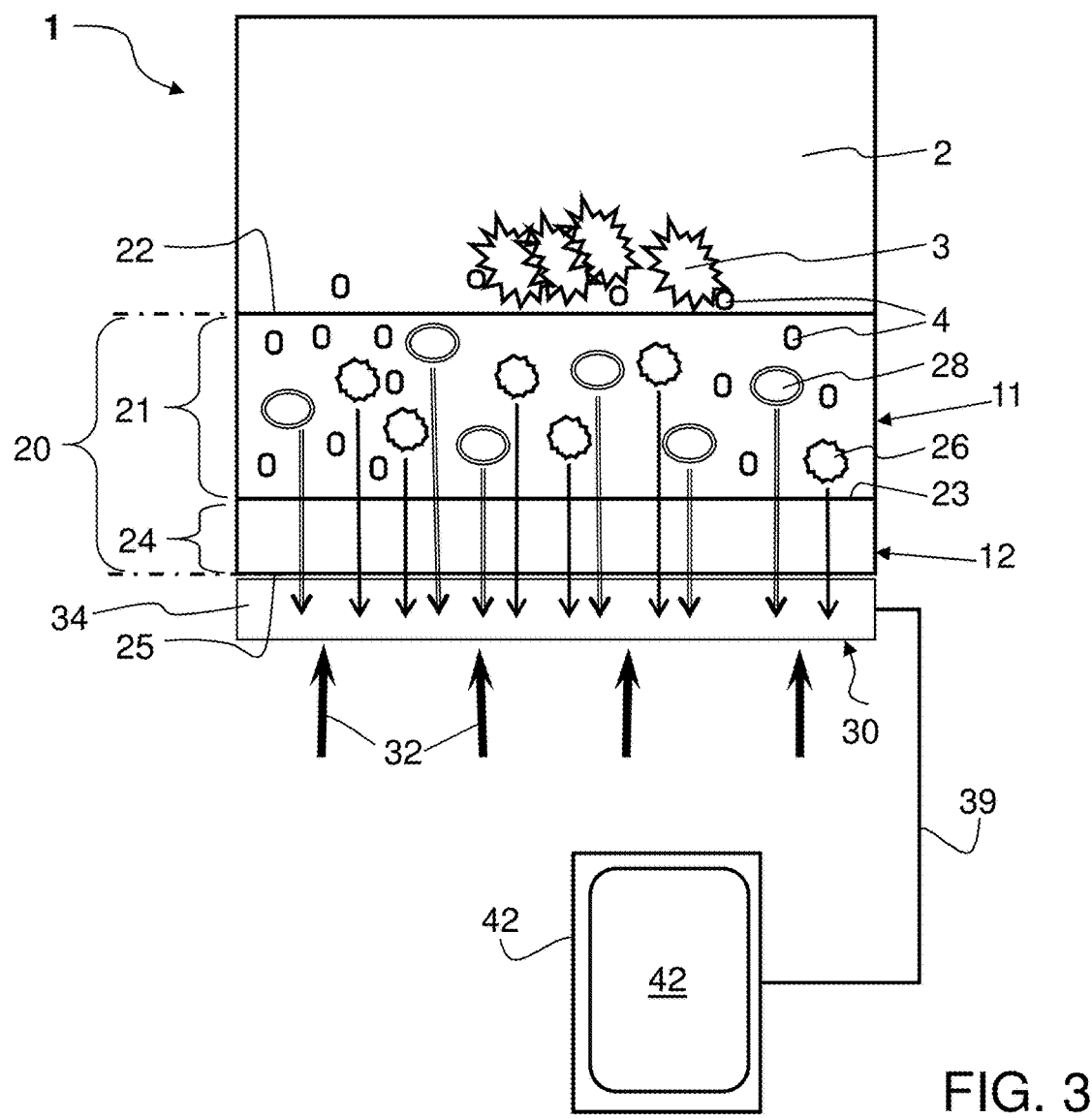
FIG. 3 is a schematic view of an arrangement for detecting microorganisms according to a further embodiment to the present invention.

FIG. 3 shows a schematic view of an alternative embodiment of the arrangement 1 of the present invention. The detection element 30 is a sensor chip 34. The sensor chip 34 is directly attached to the second free surface side 25 of the transparent read-out carrier layer 24. The sensor chip 34 receives the emission 27 of the oxygen indicator dye 26. The sensor chip 34 is in a communicative connection 39 with the evaluation unit 40. The evaluation unit 40, shown here, is a mobile device with an integrated display 42. No optic 35, as necessary in the embodiment of FIG. 2, is needed. The detected emission 27 of the oxygen indicator dye 26 in the first layer 11 (oxygen-permeable layer 21) is projected onto the sensor chip 34. The composition of the sensor foil 20 is already described in FIG. 2.

Figure 4:
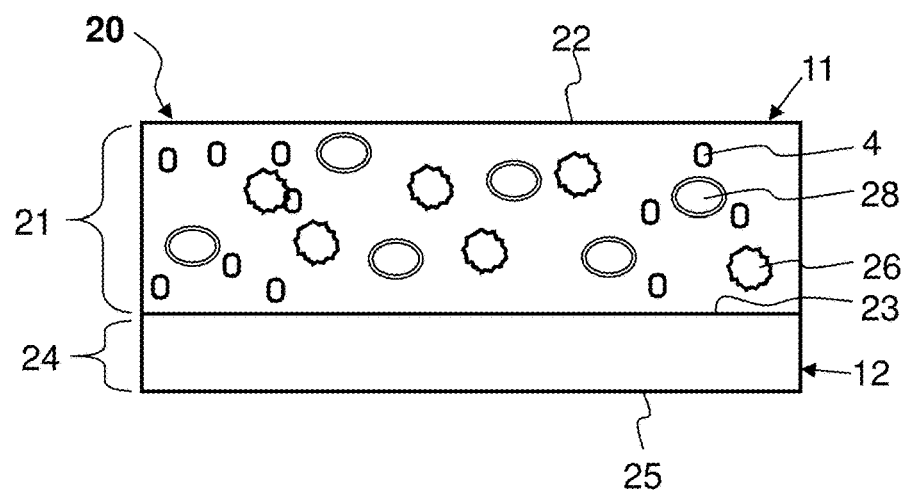
FIG. 4 is a detailed view of the sensor foil according to an embodiment to the present invention.

FIG. 4 shows a detailed view of the sensor foil 20 according to an embodiment to the present invention. According to an embodiment of the present invention, the oxygen-permeable layer 21 (first layer 11) of the sensor foil 20 comprises polyvinyl chloride.

In an embodiment of the invention, the oxygen-impermeable transparent read-out carrier layer 24 (second layer) of the sensor foil 20 comprises polyester.

In an embodiment of the invention, at least one oxygen indicator dye 26 or at least one oxygen indicator dye 26 plus at least one reference dye 28 are fluorescent, phosphorescent, luminescent, colorimetric and/or have another optical property changing over time t with respiration of oxygen 4 by the microorganisms 3.

Figure 5:
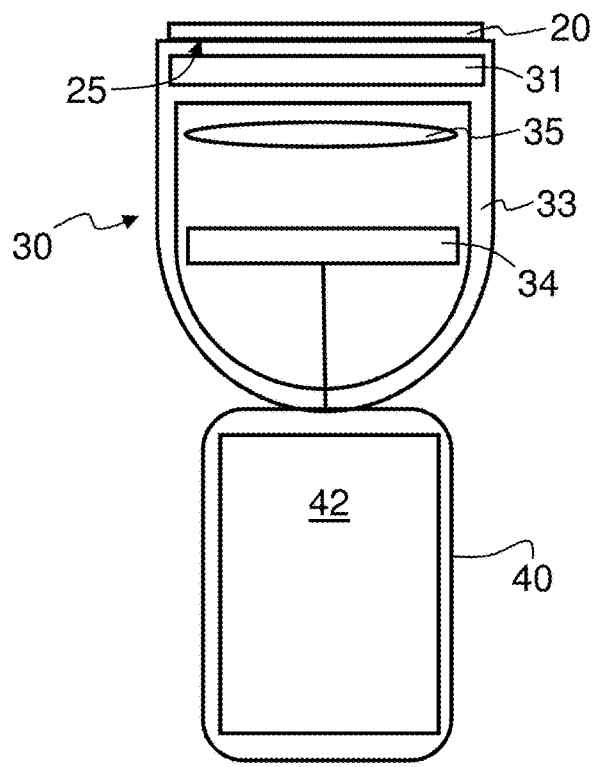
FIG. 5 is a schematic view of a detection element according to an embodiment of the present invention.

FIG. 5 shows a schematic view of a detection element 30 according to another embodiment to the present invention. In comparison to FIG. 2, in the detection element 30 according to the embodiment of FIG. 5, the evaluation unit 40 with the display 42 is communicatively attached to the detection element 30. The design of the detection element 30 is already described in FIG. 2. The evaluation unit 40, which can be, for example, a smart phone, is used as an embedded system for carrying out the evaluations of the data and information detected by the sensor foil 20. According to the evaluation, it is possible to show a 2-dimensional distribution of microorganisms 3 on the display 42 or carry out a statistical analysis of the microorganisms present on the at least one portion of the surface 2. The evaluation unit 40 can be an integrated part of the detection element 30.

Regardless of the embodiment, whether the evaluation unit 40 is an integrated part of the detection element 30 or not, the detection element 30 can be attached in a fixed or detachable manner to the second free surface side 25 of the oxygen-impermeable transparent read-out layer 24 of the sensor foil 20. This design provides a particularly compact detector element 30.

All further elements in FIG. 5 have already been described with reference to FIG. 2 in detail. The connection 39 between the detector element 30 and the evaluation unit 40 can be a hard wire connection or wireless connection.

For rather large surfaces 2 to be inspected for possible microorganisms 3, the sensor foil 20 can have respective similar extensions.

Figure 6:
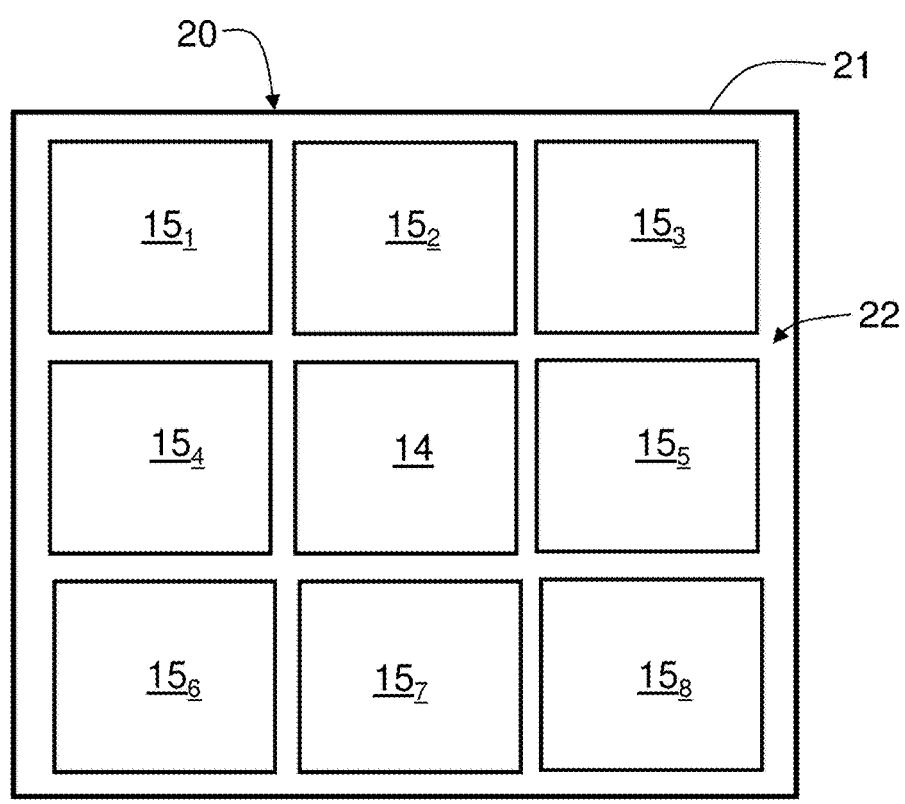
FIG. 6 is a schematic view of the first free surface side of the oxygen-permeable layer to be in contact with the possible microorganisms on the surface to be detected, according to an embodiment of the present invention.

FIG. 6 is a schematic view onto the first free surface side 22 of the oxygen-permeable layer 21 of the sensor foil 20 according to an embodiment of the present invention. The first free surface side 22 is in contact with the microorganisms 3 on the surface 2 to be detected. The first free surface side 22 of the oxygen-permeable layer 21 of sensor foil 20 carries a regular pattern of a plurality of fields $15_1$, $15_2$, ..., $15_N$, wherein each field $15_1$, $15_2$, ..., $15_N$, except at least one reference field 14, carries a substance which is antimicrobial and/or antibiotic. The arrangement of the fields $15_1$, $15_2$, ..., $15_N$ and the at least one reference field 14 shows only one possible embodiment and does not limit the arrangement of the fields $15_1$, $15_2$, ..., $15_N$ and the reference field 14 on the first free surface side 22 of the sensor foil 20. For example, each field $15_1$, $15_2$, ..., $15_N$ can carry a different type of antibiotic in order to determine their effect on the microorganisms 3.

Figure 7:
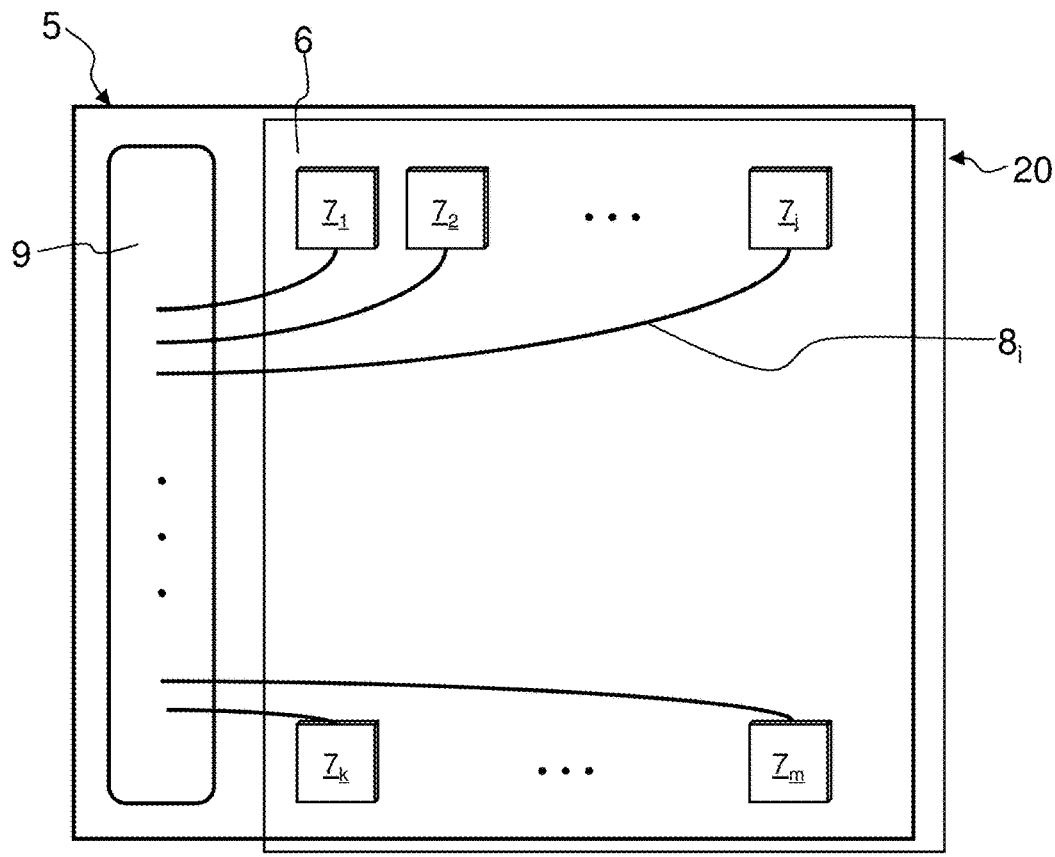
FIG. 7 is a schematic view of an embodiment of an array with a series of samples to be detected for microorganisms.

FIG. 7 is a schematic view of a further embodiment of an arrangement 1 according to the present invention. A plate 5 is provided with an array 6 of a series of samples $7_i$, i=1, ..., j, ..., k, ..., m. The individual samples $7_i$ represent individual environments 2 to be examined for possible microorganisms 3 by the method of the present invention. Each sample $7_i$ contains a probing solution with microorganisms 3, for example bacteria and/or fungi to be tested. For example, but not limited to, the samples $7_i$ contain immobilized antimicrobial substances of different concentration. A sensor foil 20 is configured so that it can cover a portion of the plate 5 with all the samples $7_i$ in an airtight manner and so that the microorganisms "breathe" directly into the oxygen-permeable layer 21 of the sensor foil 20.

A detection element 30, for example having a CMOS, is configured so that it illuminates at least a portion of the sensor foil 20 when attached to the plate 5 to excite the oxygen indicator dye 26 in the oxygen-permeable layer 21, to detect an emission 27 transmitted through the oxygen-impermeable transparent read-out layer 24 (see FIG. 2), and to read the sensor response of the sensor foil 20. Through this arrangement extremely small volumes ("Picoliter respiratory chambers") of samples $7_i$ can be produced and a time series of the response of the sensor foil 20 can be recorded, so that an oxygen consumption kinetics can be determined. For example, the minimum inhibitory concentration (MIC) based on the detected emission 27 and kinetics can be determined. This arrangement is useful for sensitivity tests and detection of resistance mechanisms in clinically relevant bacteria and yeasts.

In further embodiments, the oxygen-permeable layer 21 of the sensor foil 20 is treated and/or functionalized.

In one embodiment, the oxygen-permeable layer 21 of the sensor foil 20 is coated or soaked with antibiotics in order to determine the degree of effectiveness of the antibiotics in a series of samples $7_i$ covered with the thus treated sensor foil 20.

The antibiotics should cause reduced respiration of the microorganisms (bacteria, fungi etc.). In case the microorganisms are sensitive to the antibiotics, the detected $O_2$ values remain high over time. In case the microorganisms are less sensitive to the antibiotics, the microorganisms alter their breathing and the $O_2$ values change by consumption. In case the microorganisms are resistant to the antibiotics, the microorganisms do not change their breathing and the $O_2$ values greatly decrease by $O_2$ consumption over time.

Each sample $7_i$ is connected via a wire, cable or wireless connection $8_i$ with a circuitry 9 for sending the data to a remote or local evaluation unit (not shown).

Figure 8:
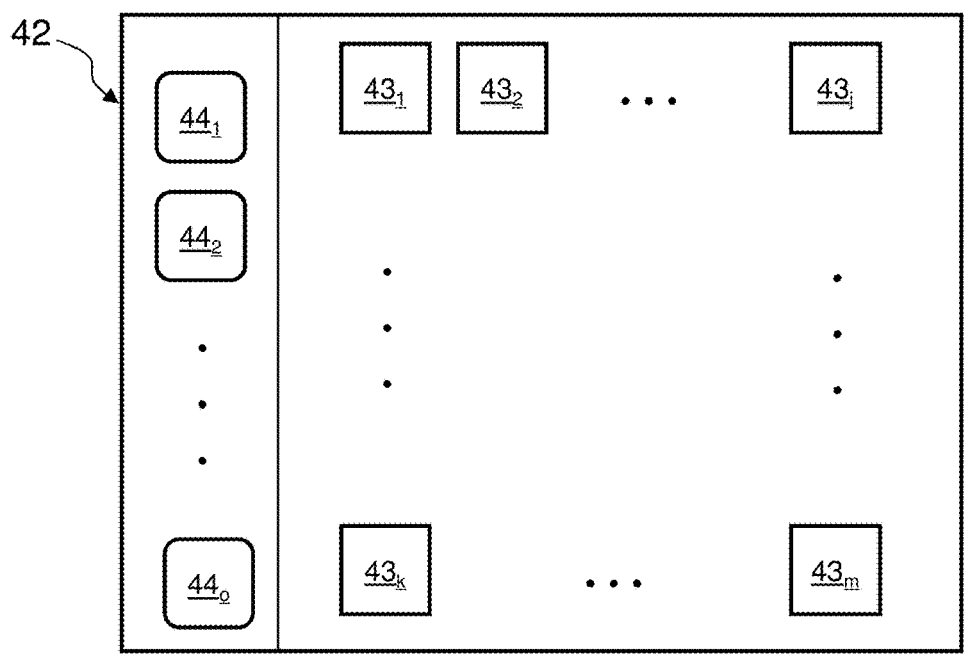
FIG. 8 is a schematic view of an embodiment of the display for showing a 2-dimensional distribution of microorganisms on the series of samples in FIG. 7.

FIG. 8 is a schematic view of an embodiment of a display 42 for showing a 2-dimensional distribution of microorganisms 3 on the series of samples $7_i$ in FIG. 5. Each sample $7_i$ is represented by a respective result image $43_i$, i=1, ..., j, ..., k, ..., m. Each result image $43_i$ shows, for example, a representative image taken by the detection element 30, which can be configured as a CCD-camera. When activating a single image icon $43_i$, for example, further results details and/or a magnified image $43_i$, are shown on display 42.

Function keys $44_n$, n=1, ..., o, enable the user to call various sub-routines in order to carry out different evaluations and/or graphical representations of the detected data. Additionally, the detection element 30 not shown can be controlled via specific function keys $44_n$.

Figure 9:
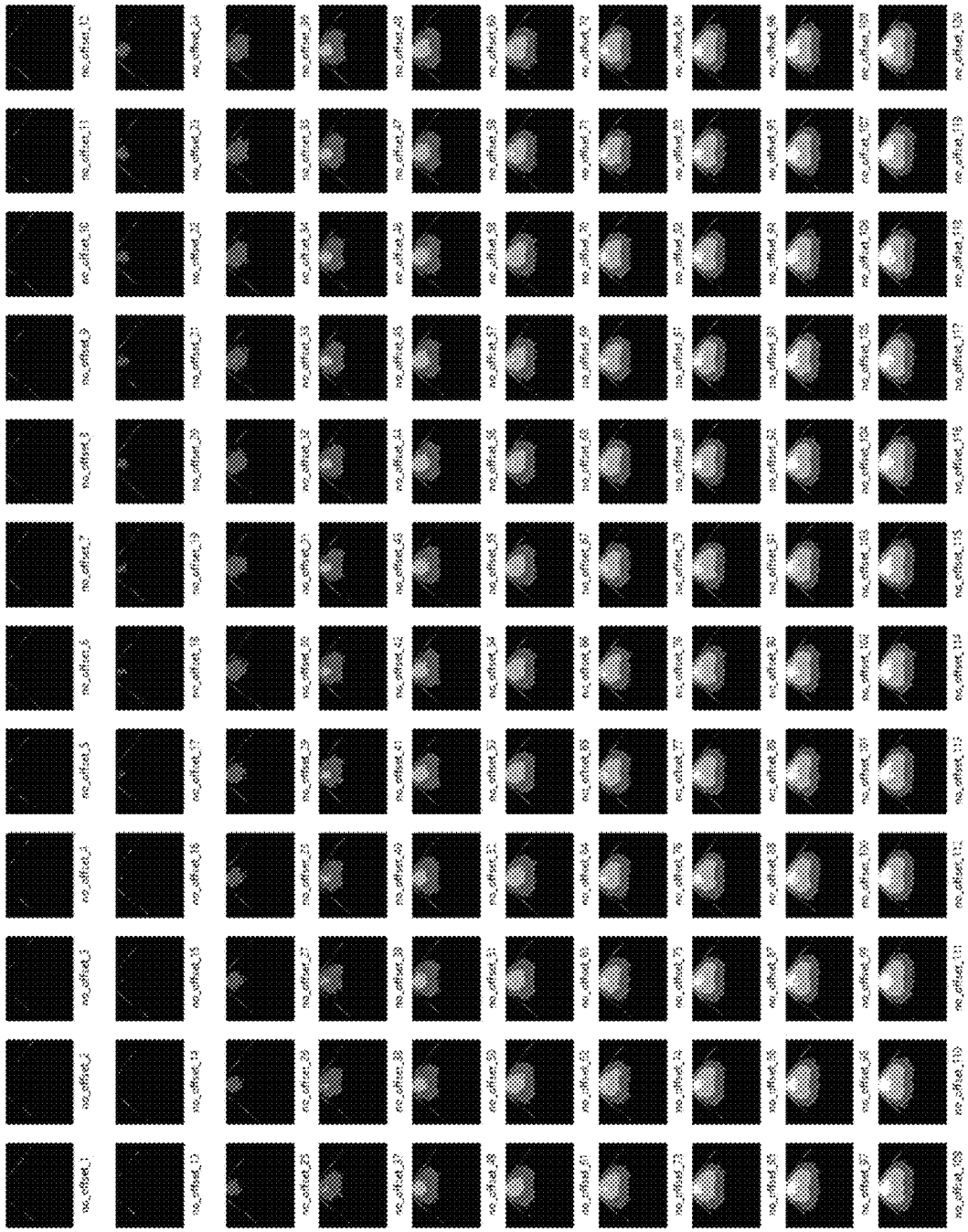
FIG. 9 is an exemplary time series of detection result images.

Thus, a time series of samples $7_i$, i=1, j, ..., k, ..., m, as to detecting microorganisms 3 on these samples $7_i$ can be recorded with the detection element 30 and displayed via a respective time series of result images $43_i$. For example, a surface partially colonized with microorganisms 3 is covered with a sensor foil 20 and read-out in fixed time intervals, for example 2 sec, as shown in FIG. 9. Hence, FIG. 9 is a time series of detection result images $43_i$.

Figure 10:
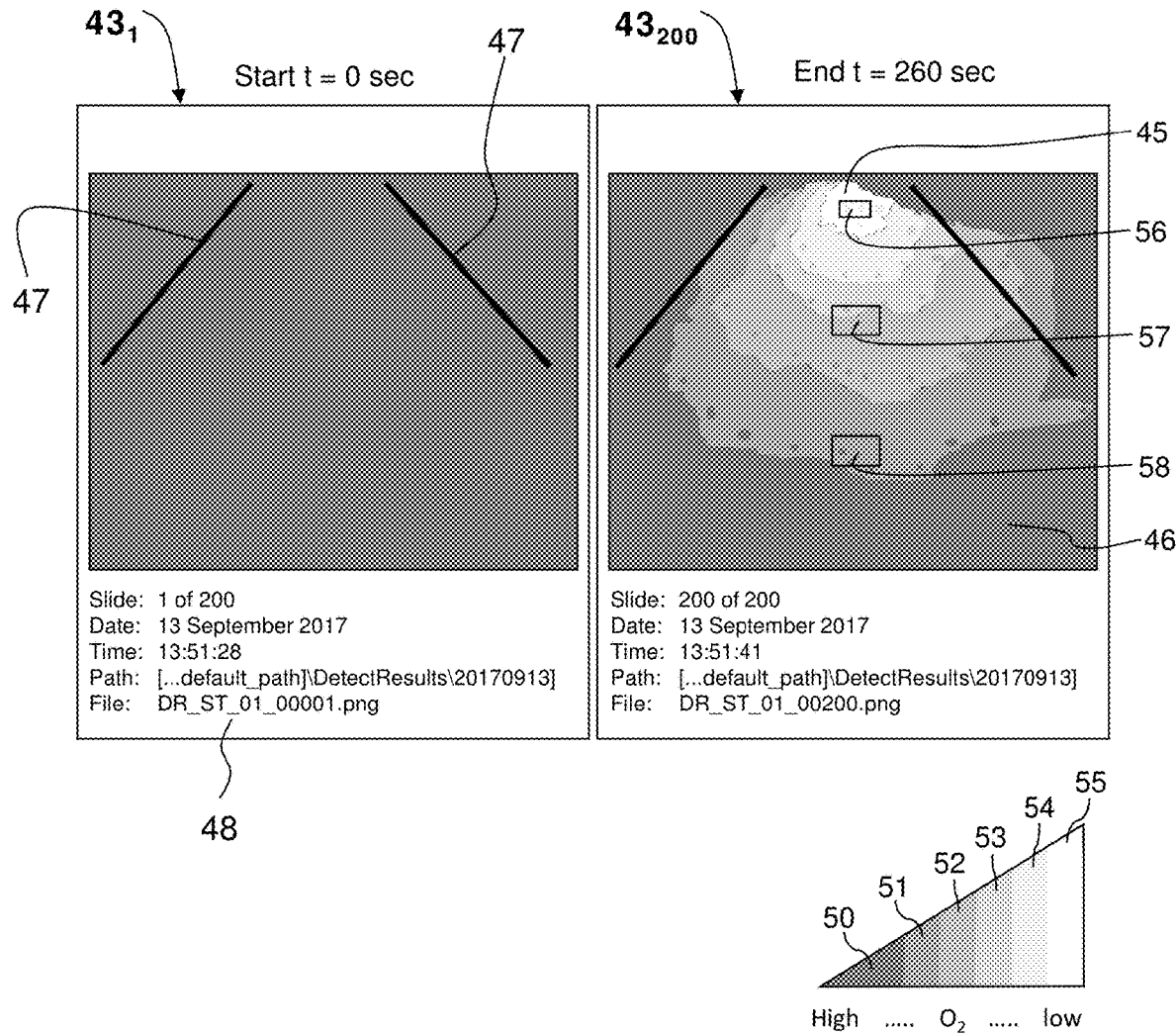
FIG. 10 shows the first and the last detection result images of an exemplary time series with 200 samples and detection result images.

FIG. 10 shows the first last detection result image $43_1$ and the last detection result image $43_{200}$ of an exemplary time series with 200 samples $7_i$, i=1, ..., 200 (see FIG. 7), and therefrom resulting m=200 detection result images $43_i$, i=1, ..., 200, as for example, shown in FIGS. 8 and 9.

In the exemplary series of samples $7_i$, each sample $7_i$, i=1, ..., 200, is provided with the same amount of microorganisms 3, a maximum amount of antibiotics or a maximum strong antibiotics is added to the first sample $7_i$, the last sample $7_{200}$ contains no antibiotics, and with increasing index i=2, ..., 199, an increasing amount of antibiotics or increasingly stronger antibiotics have been added to the respective samples $7_i$. Then the method according to the invention is applied to each of the samples $7_i$, for example as described with regard to FIG. 7, for detecting the remaining amounts of microorganisms 3 on the samples $7_i$ after the have been treated with the different amounts and/or strengths of antibiotics. At least one detection result image $43_i$ is taken of each sample $7_i$. The content of a result image $43_i$ depends on the amount of antibiotics added to the respective sample $7_i$, as will be described in the following.

In an embodiment of the invention, each $O_2$ value detected and indicating the presence or absence of microorganisms 3 by the method and/or arrangement 1 is assigned to a specific color 50, 51, ..., 55. Thus, the quantification, i.e. the amounts, of $O_2$ consumption across the respective sample $7_i$ can be visualized by means of the result images $43_i$. The colors can be, but are not limited to, a range of greys or a range of any other colors of the known continuous color spectrum. The sensor foil 20 should provide ratiometric properties accordingly. For mere explanation, in the example of FIG. 10, six distinctive separate colors 50, 51, ..., 55 have been chosen. However, in reality, the number of microorganisms 3 and hence the amount of $O_2$ usually changes across the sample to be detected in a continuous manner. Therefore, the colors selected for representation of the diverse $O_2$ amounts across the pixels of any single image $43_i$ can be taken from a continuous interval of the maximal $O_2$ value and the minimum $O_2$ value detected.

In the exemplary case of FIG. 10, light regions 45 in the last result image $43_{200}$ represent surface portions of the respective last sample $7_{200}$ where a maximum of microorganisms 3 are present, and hence, $O_2$ presence is low due to $O_2$ consumption of the microorganisms 3, represented, for example by the lightest color 55 in the chosen range of colors. Dark regions 46 in the last result image $43_{200}$ represent other surface portions of the respective last sample $7_{200}$ where the presence of microorganisms 3 is at its minimum, maybe even absent, and hence, $O_2$ presence is high, represented, for example by the darkest color 50 in the chosen range of colors. The series of result images $43_i$ thus visualize the degree of effectiveness of an antibiotic and the amounts of the antibiotic needed for reducing or even eliminating the microorganisms on the samples $7_i$ of an environment 2.

Figure 11:
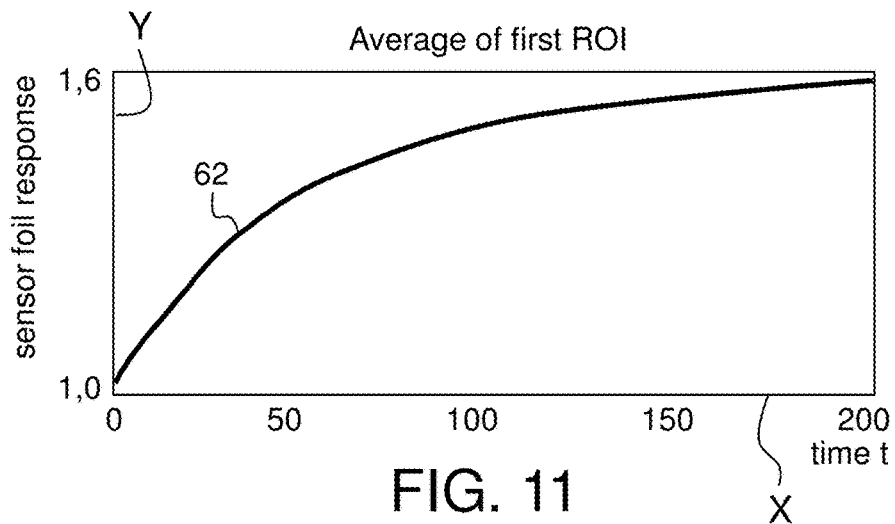
FIG. 11 is a diagram with a graph showing the sensor foil response along the time axis for a first region of interest.
Figure 12:
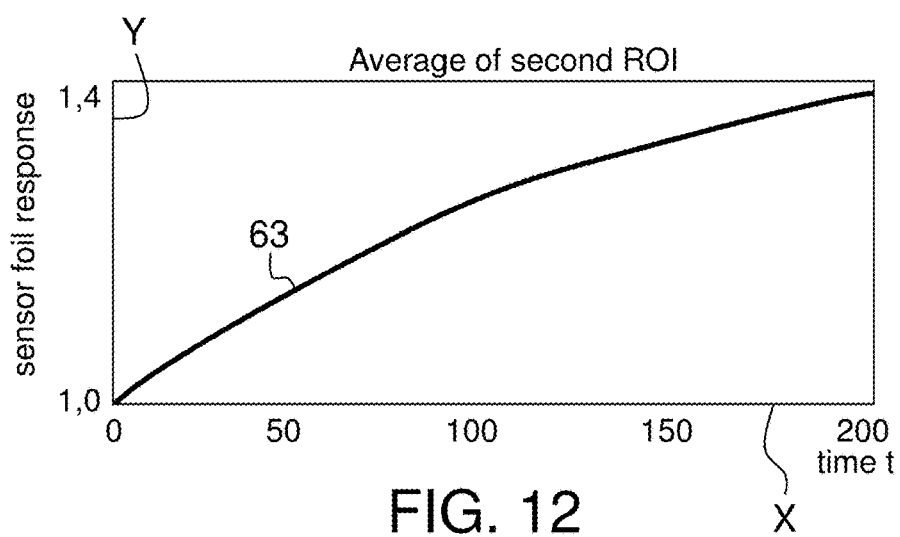
FIG. 12 is a diagram with a graph showing the sensor foil response along the time axis for a second region of interest.
Figure 13:
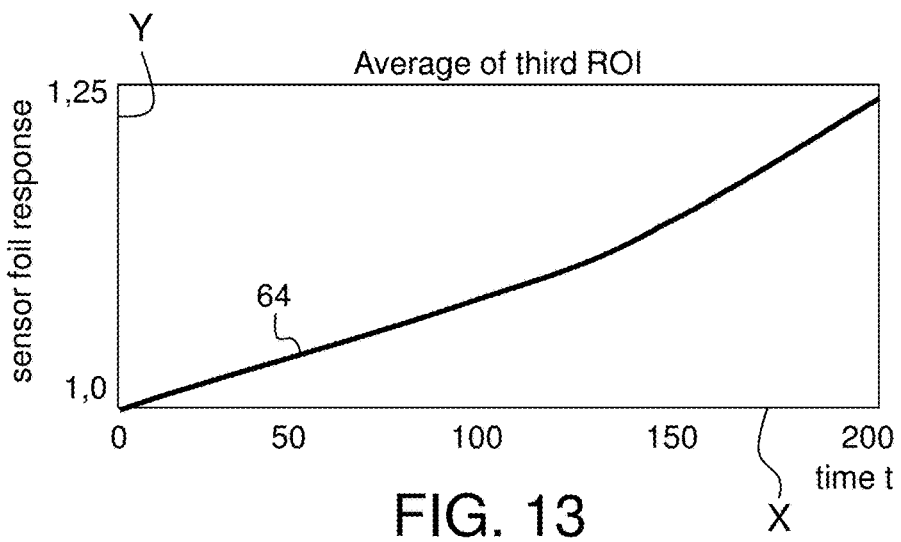
FIG. 13 is a diagram with a graph showing the sensor foil response along the time axis for a third region of interest.

In the last result image $43_{200}$, three regions of interest 56, 57, 58 are marked which are examined and described in more detail in FIGS. 11, 12, 13.

Reference sign 47 in the result images $43_i$ represents boundary lines of the surface 2 or boundaries of the sensor foil 20.

A person skilled in the art knows that any other range of colors can be chosen suitable for visualizing the amounts of $O_2$ and hence visualizing the amounts of microorganisms 3 on a sample $7_i$, without departing from the scope of the invention. A person skilled in the art also knows that in the series of samples $7_i$ and result images $43_i$, i=1, ..., m, the total number m can be less or more than 200 and/or the total number m of result images $43_i$ can be equal or greater than the total number m of samples $7_i$ and/or the number of regions of interest 56, 57, 58 can be different from three without departing from the scope of the invention.

Description data 48, such as, but not limited to, the index i of a respective result image (slide) $43_i$ (for example 1 and 200), the total number of result images (slides) $43_i$ (for example 200), the date and time of the result images $43_i$, the path where the file of the result image (slide) $43_i$ is saved, and the and file name of the result image (slide) $43_i$, can be added to each result image $43_i$ automatically by a respective software.

FIG. 11 is a diagram with a graph 62 showing the response of the sensor foil 20 as a function of time t along the X-axis X for the first region of interest 56 (ROI) in the last detection result image $43_{200}$ of FIG. 10. Graph 62 shows a strong decrease of oxygen $O_2$ which means a high $O_2$ respiration rate which reaches a saturation after a certain period of time, which in turn means a high number of microorganisms in average present in the first region of interest 56. The scale of the Y-axis Y is in arbitrary units.

FIG. 12 is a diagram with a graph 63 showing the response of the sensor foil 20 of FIG. 10 as a function of time t along the X-axis X for the second region of interest 57 in the last detection result image $43_{200}$ of FIG. 10. Graph 63 shows a mediate decrease of oxygen $O_2$ which means a mediate $O_2$ respiration rate. The scale of the Y-axis is in arbitrary units and the range of the Y-axis Y of FIG. 12 is lower than the range of the Y-axis Y in FIG. 11. This means in turn that a mediate number of microorganisms in average is present in the second region of interest 57.

FIG. 13 is a diagram with a graph 64 showing the response of the sensor foil 20 of FIG. 10 as a function of time t along the X-axis X for the third region of interest 58 in the last detection result image $43_{200}$ of FIG. 10. Graph 64 shows a low decrease of oxygen $O_2$ which means a low $O_2$ respiration rate. The scale of the Y-axis is in arbitrary units and the range of the Y-axis Y of FIG. 13 is lower than the range of the Y-axis Y in FIG. 12. This means that a low number of microorganisms in average is present in the third region of interest 58.

For example, in FIGS. 11, 12 and 13 a ratiometric sensor foil 20 can be used which, for example ratiometric with regard to the colors red and green.

In another embodiment of the inventive arrangement and method, bacteria as microorganisms are detected on a surface via determining pH value changes. In general, most bacteria generate acids or protons during metabolism. Acids and protons influence the pH value of an aqueous phase. Bacterial growth is a spatially diverged phenomenon. Therefore 2-dimensional information has to be gained, which is achieved in the present invention through the result images 43 as response of the sensor foil 20. For example, pH changes caused by bacterial metabolism can be observed via optical pH sensor foils 20.

For example, bacteria can be detected via determining pH value changes by using a planar optical sensor foil 20. A surface of a sample that is suspicious to contain (a relevant amount of) bacteria is covered with a planar optical pH sensor foil 20. The planar optical pH sensor foil 20 can consist of at least one fluorescent or colorimetric pH indicator that results in a pH dependent signal change. Further the planar optical pH sensor foil 20 can consist of a referencing element that enables referenced signal read out. Planar optical pH sensor foils 20 should comprise a certain amount of humidity for enabling a bacteria dependent pH-change. The signal change is read out in a spatially derived manner, e.g. with an array detector or a camera. pH changes can be monitored either as signal change after a certain period of time or in a time dependent experiment.

Spatially and time dependent signal changes in the response of the sensor foil 20 enable to locate regions in a region of interest in a sample with pH changes by bacterial presence or growth. Signal thresholds of recorded pH changes can be used to determine positive and negative results. A color system can be used for the result images 43 resulting from the response of the sensor foil 20 as described above in order to visualize the results, i.e. the degree of presence or absence of bacteria in the sample. Metabolism activators can be used in the oxygen-permeable layer 21 of sensor foil 20 to enhance pH changes caused by bacterial growth and metabolism.

In another embodiment of the inventive arrangement and method, bacteria as microorganisms are detected on a surface via determining pCO2 levels by using a pCO2 sensitive sensor foil analogous to the respiration described above.

Figure 14:
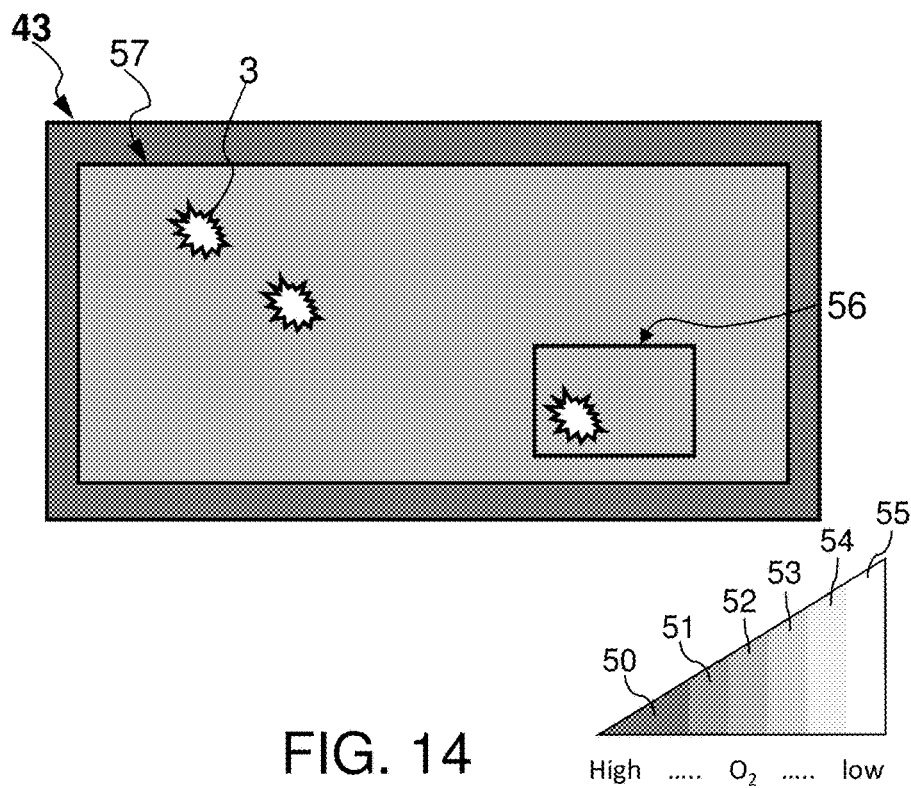
FIG. 14 is a schematic view of another example of a response of a sensor foil according an embodiment of the invention for a sample, wherein two exemplary regions of interest are selected.
Figure 15:
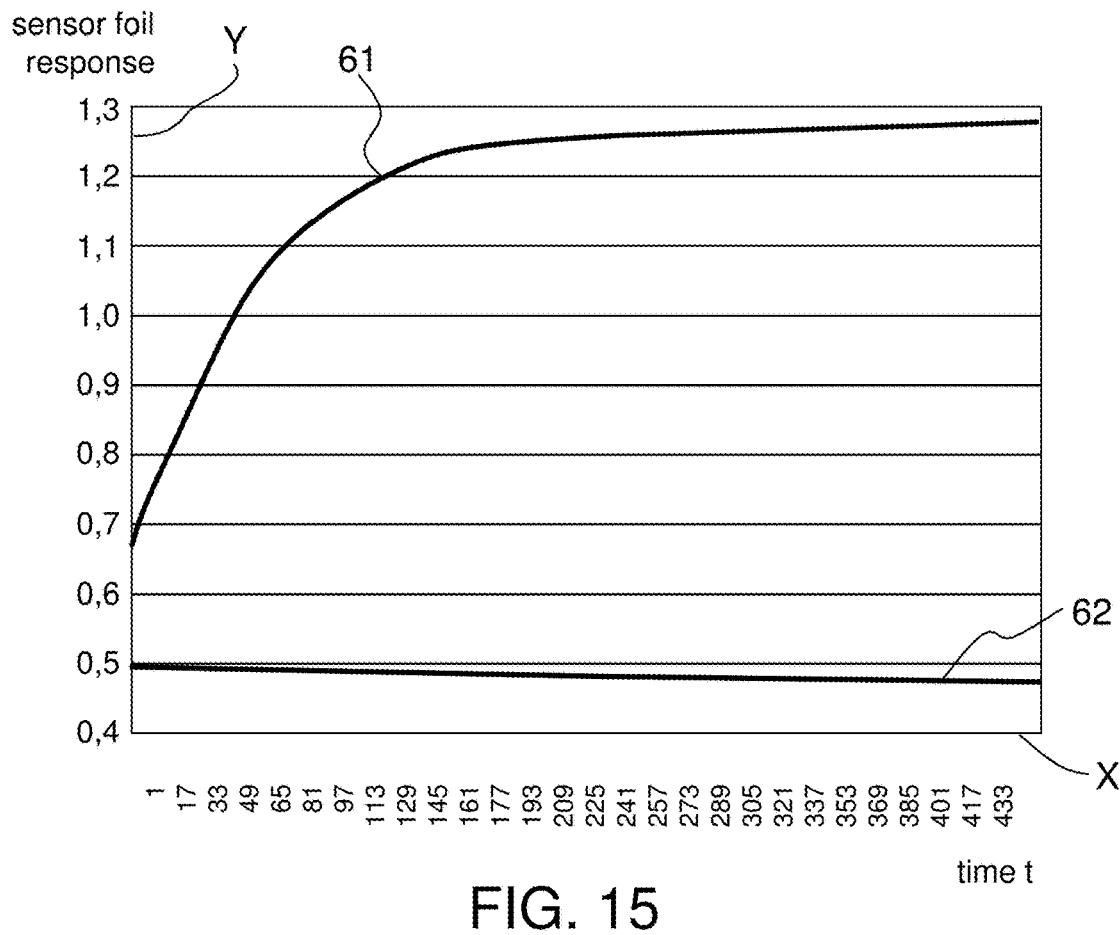
FIG. 15 is a diagram with two graphs regarding the two exemplary regions of interest in FIG. 14.

FIG. 14 is a schematic view of another example of a response of a sensor foil 20 according an embodiment of the invention for a sample, wherein two exemplary regions of interest 56, 57 are selected in a result image 43. FIG. 15 is a diagram with two graphs 61, 62 regarding the two exemplary regions 56, 57 of interest in FIG. 14. The first graph 61 shows the progress of the response of the exemplary sensor foil 20 as to the first region of interest 56, and thereby the progress of oxygen $O_2$ amounts in the first region of interest 56 in the sample as a function of time t along the X axis X. The first region of interest 56 is an area of the surface which is covered by the sensor foil where the population of microorganisms is high. Accordingly, the second graph 62 shows the progress of the response of the exemplary sensor foil 20 as to the second region of interest 57, and thereby the progress of oxygen $O_2$ amounts in the second region of interest 57 in the sample as a function of time t along the X axis X. In a time series, the result image 43 depicted in FIG. 14 is repeatedly recorded at certain time intervals and is represented in the two graphs 61, 62 in FIG. 15.

As described before, the sensor foil 20 is "charged" in ambient air before it is applied to the surface (oxygen partial pressure is identical to the environment inside the sensor and thus "high"). In regions where microorganisms 3 are not present, the oxygen partial pressure remains high, i.e. no breathing and no $O_2$ consumption occur, which can be represented, for example, by the color 50 blue or the darkest grey in the result image 43. In regions where microorganisms 3 are present, the oxygen partial pressure is reduced by breathing after a short time, i.e. respiration and consumption $O_2$ consumption occur, which can be represented, for example, by the color 55 yellow or white in the result image 43. If the above-described embodiment of an arrangement 1 with an OLED is used directly on the sensor foil 20, the user sees this colored result image 43 directly via the OLED. Therefore, in this embodiment, no optical read-out system, like for example a camera, is required to visualize microorganisms on the surface of the sample 7 to be tested.

Evaluating the mean value over the entire sensor foil 20, i.e. essentially over the second region of interest 57, results in little change if only a few (microscopic small) microorganisms are present within this large region of interest 57. The partial strong change in small regions, like for example in the small region of interest 56, has little effect on the average value of a large region of interest, like for example of the large region of interest 57. This type of detection is typical for point measurements in which millimeter-sized points or spots are read "average" with an optical fiber.

If, however, the response of the sensor foil 20 is only evaluated around the spots emerging from oxygen consumption in small regions of interest like region 56, the oxygen partial pressure change at microscopically small regions can be evaluated with a significant change in the sensor response. For example, one uses the core property of a sensor, i.e. detecting at very high spatial resolution due to individual dyes, and of a camera, i.e. detecting two-dimensionally resolved sensor responses due to single pixels.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

LIST OF REFERENCE NUMERALS 1 arrangement
2 surface
3 microorganism
4 oxygen ($O_2$)
5 plate
6 array
$7_i$ sample, i=1, . . . , j, . . . , k, . . . , m
$8_i$ wire, cable or wireless connection, i=1, . . . , j, . . . , k, . . . , m
9 circuitry
11 first layer
12 second layer
14 reference field
$15_1, 15_2, \ldots, 15_N$ field
20 sensor foil
21 oxygen-permeable layer (sensitive layer, polymer layer)
22 first free surface side (oxygen-permeable contact side to microorganisms)

23 read-out surface side
24 oxygen-impermeable at least partially transparent read-out carrier layer (polyester support)
25 second free surface side (oxygen-impermeable and at least partially transparent read-out side)
26 oxygen indicator dye
27 emission of oxygen indicator dye
28 reference dye
29 emission of reference dye
30 detection element
31 light source (light emitting element)
32 excitation light
33 housing
34 detector chip, sensor chip
35 optic
36 transmission circuitry
38 detection device
39 connection
40 evaluation unit
42 display
$43_i$ result image (slide), i=1, . . . , j, . . . , k, . . . , m
$44_n$ function key, n=1, . . . , o
45 image region with microorganisms present
46 image region with microorganisms absent
47 boundary line
48 description data
50 color
51 color
52 color
53 color
54 color
55 color
56 first region of interest
57 second region of interest
58 third region of interest
60 graph
61 graph
62 graph
63 graph
64 graph
Q1 query of examining next portion of environment
S1 step of covering at least a portion of the environment to be detected with a sensor foil in an airtight manner
S2 step of placing a detection element in relation to the sensor foil
S3 step of sending an excitation light through an oxygen-impermeable at least partially transparent read-out carrier layer of the sensor foil to the oxygen-permeable layer of the sensor foil
S4 step of detecting an emission of the oxygen indicator dye transmitted through the oxygen-impermeable at least partially transparent read-out carrier layer of the sensor foil by the detection element over a period of time
S5 step of imaging the detected emission
S6 step of post-processing the detected emission
t time
X X-axis
Y X-axis

What is claimed is:

1. An arrangement for detecting microorganisms on a surface of any topology under in situ examination, the arrangement comprising:
a sensor foil having an oxygen-permeable layer doped with an oxygen indicator dye and loaded with oxygen, and an oxygen-impermeable at least partially transparent read-out carrier layer carrying the oxygen-permeable layer, the sensor foil being thin and flexible to attach directly to at least one portion of the surface any topology carrying the microorganisms, the sensor foil being configured such that it attaches directly to the at least one portion of the surface of any topology in an airtight sealed manner, the surface of any topology being that of an item, a human or an animal;
the oxygen-permeable layer of the sensor foil having a first free surface side, and the oxygen-impermeable at least partially transparent read-out carrier layer of the sensor foil having a second free surface side oppositely of the first free surface side, the first free surface side of the oxygen-permeable layer adapted to attach directly in an airtight sealed manner to the microorganisms on the at least one portion of the surface of any topology;
thereby blocking re-oxygenation of the oxygen-permeable layer of the sensor foil;
a detection element arranged in optical relation to the sensor foil for receiving an emission of the oxygen indicator dye when the dye is in an excited state, the emission being transmitted through the oxygen-impermeable at least partially transparent read-out carrier layer, the detection element serving to detect an oxygen decrease in the oxygen-permeable layer of the sensor foil;
an evaluation unit for calculating a graphical or statistical representation of the received emission; and
a display connected to the evaluation unit and adapted to display the graphical or statistical representation of the received emission, the representation being indicative of a presence and concentration of the microorganisms on the at least one portion of the surface of any topology under in situ examination, which is airtight sealed by the first free surface side of the oxygen-permeable layer of the sensor foil in the airtight sealed manner.

2. The arrangement as claimed in claim 1, further comprising a light source providing excitation light and being placed in optical relation to the sensor foil so that excitation light can reach the oxygen-permeable layer.

3. The arrangement as claimed in claim 1, wherein the detection element is a sensor chip directly attached to the at least partially transparent read-out carrier layer for receiving the emission of the oxygen indicator dye, and wherein the sensor chip is in a communicative connection with the evaluation unit.

4. The arrangement as claimed in claim 1, wherein the detection element is a detection device having at least one detector chip and an optic held in position by a housing, wherein the optic images the emission of the oxygen indicator dye transmitted through the oxygen-impermeable at least partially transparent read-out layer of the sensor foil onto the detector chip and the detector chip is in a communicative connection with the evaluation unit.

5. The arrangement as claimed in claim 4, wherein the detection device encompasses at least one light source adapted to direct the excitation light through the oxygen-impermeable at least partially transparent read-out carrier layer to the oxygen-permeable layer to excite the oxygen indicator dye in the oxygen-permeable layer by the excitation light and to emit the emission.

6. The arrangement as claimed in claim 4, wherein the detection device is attached in a fixed or detachable manner to the second free surface side of the oxygen-impermeable at least partially transparent read-out layer of the sensor foil.

7. A bendable and flexible sensor foil for detecting microorganisms on a surface of any topology of an item, a human or an animal under in situ examination, the sensor foil comprising:
- an oxygen-permeable layer doped with an oxygen indicator dye and loaded with oxygen, the oxygen-permeable layer having a first free surface side adapted to attach directly in an airtight sealed manner to at least one portion of the surface of any topology under in situ examination, thereby blocking re-oxygenation of the oxygen-permeable layer; and
- an oxygen-impermeable at least partially transparent read-out carrier layer carrying the oxygen-permeable layer;
- wherein the sensor foil is thin and flexible to cause the first free surface side of the oxygen-permeable layer of the sensor foil to attach directly to at least one portion of the surface of any topology of an item, a human or an animal in an airtight sealed manner, the first free surface side being configured such that it attaches directly to the at least one portion of the surface of any topology carrying the microorganisms in an airtight sealed manner, and wherein direct airtight sealed attachment between the oxygen-permeable layer and the surface of any topology in in situ examination allows for detection of the microorganisms based on an oxygen decrease in the oxygen-permeable layer of the sensor foil.

8. The sensor foil as claimed in claim 7, wherein the first free surface side of the oxygen-permeable layer of sensor foil carries a regular pattern of a plurality of fields, wherein each field, except one, contains a different type of an antibiotic.

* * * * *